(12) United States Patent
Heinks et al.

(10) Patent No.: US 7,401,495 B2
(45) Date of Patent: *Jul. 22, 2008

(54) ACTIVITY MONITORING

(75) Inventors: Carsten Heinks, Eindhoven (NL); Peter Tjin Sjoe Kong Tsang, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 11/680,794

(22) Filed: Mar. 1, 2007

(65) Prior Publication Data

US 2007/0193352 A1 Aug. 23, 2007

Related U.S. Application Data

(62) Division of application No. 10/537,881, filed on Jun. 7, 2005, now Pat. No. 7,204,145.

(30) Foreign Application Priority Data

Dec. 10, 2002 (EP) .................. 02080217
Nov. 21, 2003 (WO) .................. PCT/IB03/005334

(51) Int. Cl.
*G01C 25/00* (2006.01)
*G12B 13/00* (2006.01)

(52) U.S. Cl. .................. 73/1.77; 73/504.02; 73/1.37; 73/1.38; 73/504.16; 33/318

(58) Field of Classification Search .................. 73/510, 73/514.34, 865.1, 865.3, 1.01; 235/116; 600/595
See application file for complete search history.

(56) References Cited

U.S. PATENT DOCUMENTS

| | | | | |
|---|---|---|---|---|
| 5,573,013 A * | 11/1996 | Conlan | .................. | 600/595 |
| 5,721,427 A * | 2/1998 | White et al. | .................. | 250/252.1 |
| 6,122,960 A * | 9/2000 | Hutchings et al. | .................. | 73/493 |
| 6,201,476 B1* | 3/2001 | Depeursinge et al. | .................. | 340/573.1 |
| 6,280,409 B1* | 8/2001 | Stone et al. | .................. | 604/67 |
| 6,478,736 B1* | 11/2002 | Mault | .................. | 600/300 |
| 6,491,647 B1* | 12/2002 | Bridger et al. | .................. | 600/585 |
| 6,833,974 B2* | 12/2004 | Koso et al. | .................. | 360/78.05 |
| 7,204,145 B2* | 4/2007 | Heinks et al. | .................. | 73/510 |
| 2002/0109600 A1* | 8/2002 | Mault et al. | .................. | 340/573.1 |
| 2002/0116080 A1* | 8/2002 | Birnbach et al. | .................. | 700/66 |
| 2003/0226695 A1* | 12/2003 | Mault | .................. | 177/25.16 |
| 2006/0255955 A1 | 11/2006 | O'Connor et al. | | |

FOREIGN PATENT DOCUMENTS

| | | |
|---|---|---|
| EP | 0299667 | 1/1898 |
| WO | WO0152718 | 7/2001 |
| WO | WO0189365 | 11/2001 |

* cited by examiner

*Primary Examiner*—Hezron E. Williams
*Assistant Examiner*—Samir M. Shah

(57) ABSTRACT

An activity monitor is provided that corrects for the effects of motion external to the entity being monitored. For example, the activity monitor can overcome the effects of vehicular travel.

12 Claims, 4 Drawing Sheets

ACTIVITY MONITORING

CROSS REFERENCE TO RELATED APPLICATION

This is a divisional of application Ser. No. 10/537,881, filed Jun. 7, 2005 now U.S. Pat. No 7,204,145.

The present invention relates to activity monitoring, and in particular, but not exclusively to, activity monitoring of a human being.

The physical activity of a human being is an important determinant of its health. The amount of daily physical activity is considered to be a central factor in the etiology, prevention and treatment of various diseases. Information about personal physical activity can assist the individual in maintaining or improving his or her functional health status and quality of life.

A known system for monitoring human activity is described in the article "A Triaxial Accelerometer and Portable Data Processing Unit for the Assessment of Daily Physical Activity", by Bouten et al., IEEE Transactions on Biomedical Engineering, Vol. 44, NO. 3, March 1997.

According to the known system a triaxial accelerometer composed of three orthogonally mounted uniaxial piezoresistive accelerometers is used to measure accelerations covering the amplitude and frequency ranges of human body acceleration. An individual wears the triaxial accelerometer over a certain period of time. A data processing unit is attached to the triaxial accelerometer and programmed to determine the time integrals of the moduli of accelerometer output from the three orthogonal measurement directions. These time integrals are summed up and the output is stored in a memory that can be read out by a computer. The output of the triaxial accelerometer bears some relation to energy expenditure due to physical activity and provides as such a measure for the latter.

The known system allows for measurement of human body acceleration in three directions. Using state of the art techniques in the field of integrated circuit technology the accelerometer can be built small and lightweight allowing it to be worn for several days or even longer without imposing a burden to the individual wearing it.

However, the known system has the considerable drawback that "external" motion factors, such as travelling in a vehicle, are recorded in addition to the direct motion of the individual or object. In the case of a human individual only the direct motion is usually of interest, since it is the physical activity of the individual that is important.

It is therefore desirable to provide an activity monitor that can overcome these disadvantages.

According to one aspect of the present invention, there is provided an activity monitor comprising a measurement unit including a plurality of motion sensors operable to produce respective sensor signals indicative of motion experienced thereby; and a processor operable to receive the sensor signals from the measurement unit and to process the signals in accordance with a predetermined method, wherein the processor is operable to apply a correction calculation to the sensor signals, in order to remove external motion effects from the sensor signals.

FIG. 1 shows a block diagram schematically showing the components of a system embodying one aspect of the present invention;

FIG. 2 schematically shows the orthogonal position of three accelerometers;

Figure 1:
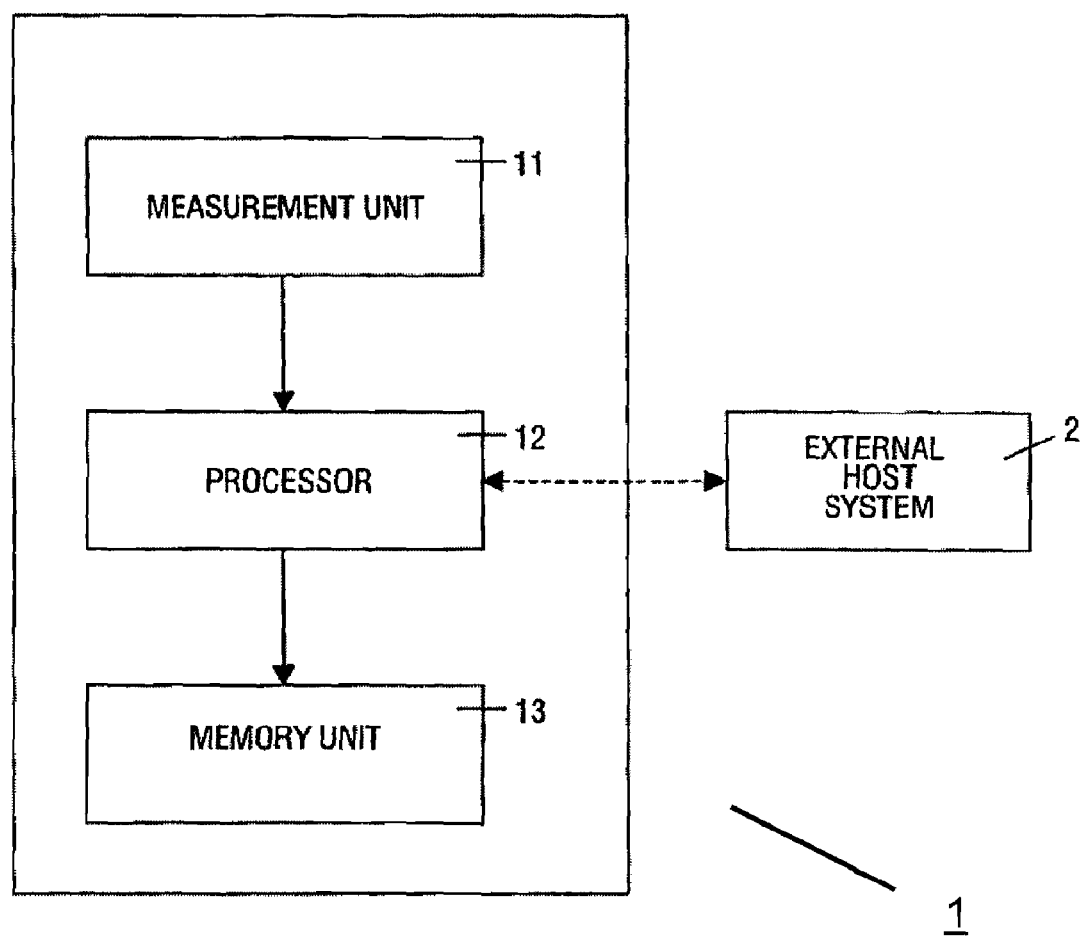

FIG. 1 illustrates an activity monitor 1 embodying one aspect of the present invention. The activity monitor 1 comprises a measurement unit 11, a processor 12, and a memory unit 13. The measurement unit 11 is operable to produce data signals indicative of the motion of the activity monitor 1, and to supply those data signals to the processor 12. The processor 12 is operable to process the data signals output from the measurement unit 11, and is able to store the data signals, or the results of the processing, in the memory unit 13. Data can be transferred between the processor 12 and the memory unit 13. The processor 12 is also able to be connected to an external host system 2, which can be a personal computer (PC) or other appropriate systems. The external host system 2 can be used to perform additional processing of the data held in the activity monitor 1.

In use, the activity monitor 1 is attached to the object to be monitored. For purposes of illustration in the following it is assumed that the object is a human individual, although it is clearly possible to apply such an activity monitor for any object. The activity monitor is attached to the individual or object for a certain time period.

The measurement unit 11 comprises three accelerometers which are arranged in mutually orthogonal directions. The accelerometers output data signals, which are indicative of the respective accelerations experienced by the accelerometers. The three accelerometers are arranged orthogonal to one another in a conventional manner.

On an individual, these directions are formed "antero-posterior", "medio-lateral" and "vertical", that are denoted as x, y and z, respectively. The accelerometers comprise strips of piezo-electric material that is uni-axial and serial bimorph. The strips are fixed at one end thereof.

The piezo-electric accelerometers act as damped mass-spring systems, wherein the piezo-electric strips act as spring and damper. Movements of the strips due to movement of the individual generate an electric charge leading to a measurement of a data signal. In case of human movements the frequency of the data signals lies in the range of 0.1-20 Hz. The amplitude of the data signals lies between −12 g and +12 g. These numbers are discussed in more detail in the article mentioned earlier. Suitable piezo-electric materials to measure such data signals are known to a person skilled in the art.

Figure 2:
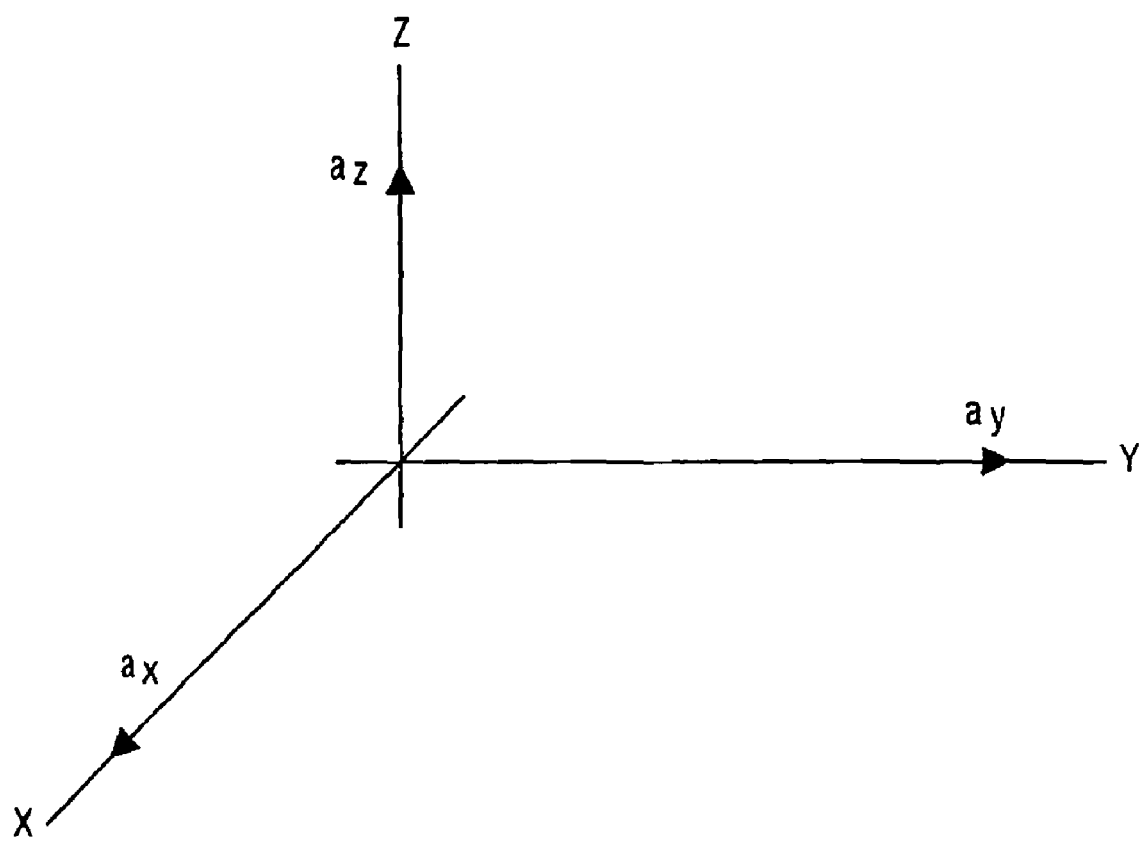

FIG. 2 illustrates the orthogonal output of the three accelerometers of the measurement unit 11. The outputs are termed $a_x$, $a_y$ and $a_z$ respectively.

In the present invention, the "external" effects of, for example, vehicle travel, are compensated for.

Figure 3:
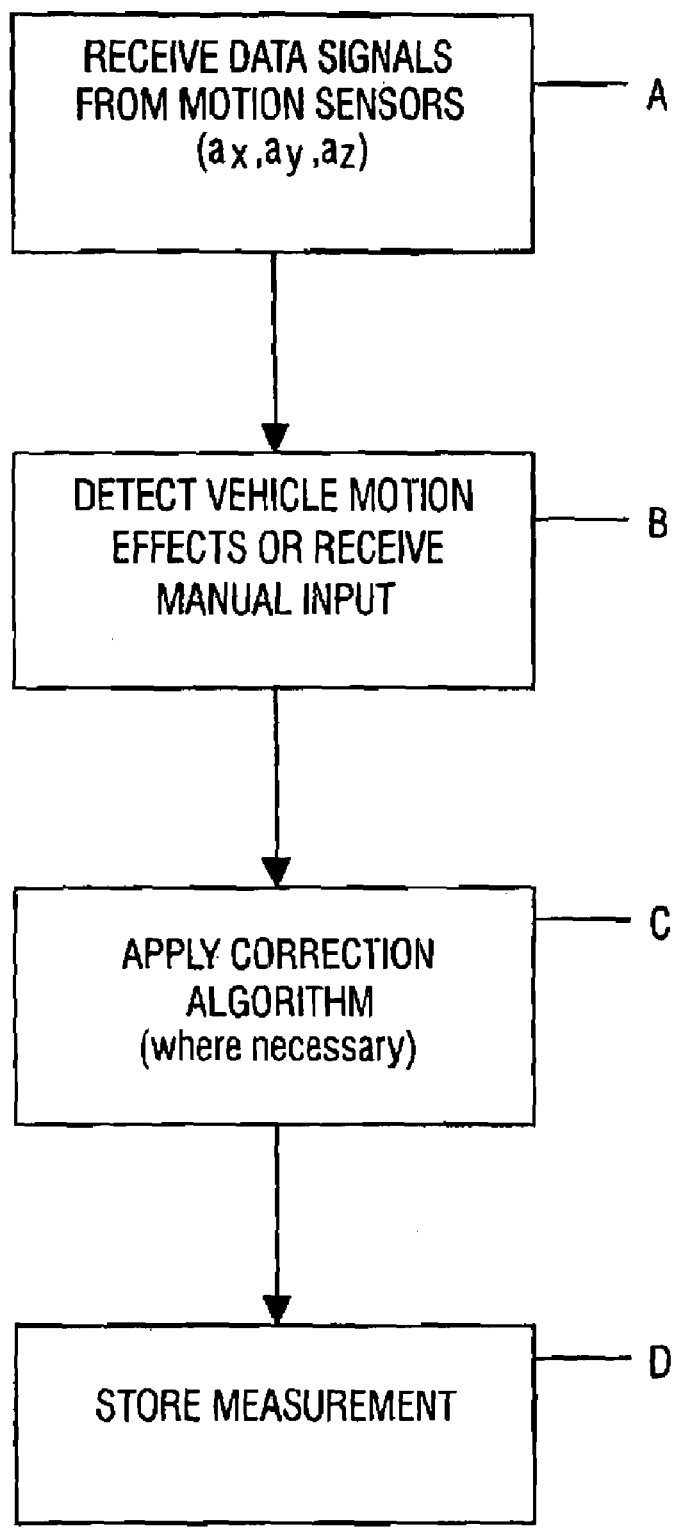
FIG. 3 shows a flow diagram of the steps of a method embodying another aspect of the present invention.

FIG. 3 illustrates a method embodying the present invention, and at step A signals are received from the motion sensors by the processor 12. At step B, the processor 12 determines whether the input sensor signals exhibit characteristics which are indicative of vehicle, or other external motion. Alternatively, the processor 12 can receive a manual intervention from the user of the device, for example in the form of a button activated on the device. Where the manual button is activated, or where the processor 12 detects external vehicle motion, a correction algorithm is applied to the sensor signals in step C, in order to remove the effects of the vehicle's motion. At step D, the corrected signals can then be stored in the memory 13.

Figure 4:
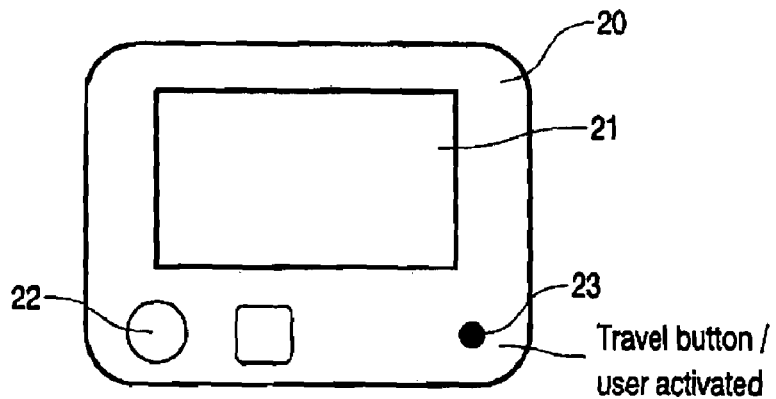
FIG. 4 illustrates a device embodying the present invention.

FIG. 4 illustrates one device embodying the present invention. The device 20 includes a display area 21, for displaying information indicative of the motion of the device. The device 20 is also provided with various control buttons 22. In one embodiment of the present invention, the device 20 is also provided with a user activated travel button 23, which is used to indicate to the device that the user is subject to external motion effects.

Figure 5:
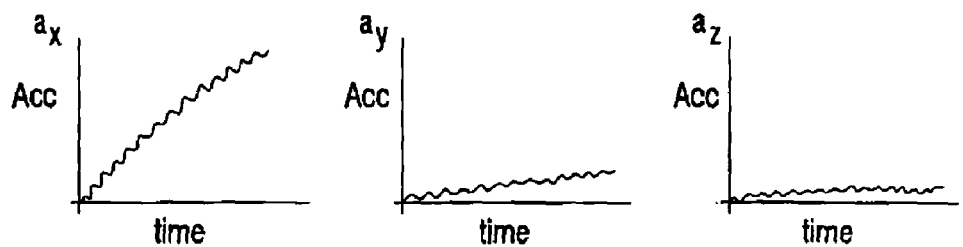
FIG. 5 illustrates motion sensor outputs.

FIG. 5 illustrates the possible variation over time of outputs from the motion sensors of the measurement unit 11. Signals related to travelling in a vehicle, for example, are generally smoother and less shaky than signals associated with an individual's physical activity. In addition, external effects often also have periodic vibrations, and so it is possible to detect such signals and to switch to a mode in which the external effects are cancelled.

Figure 6:
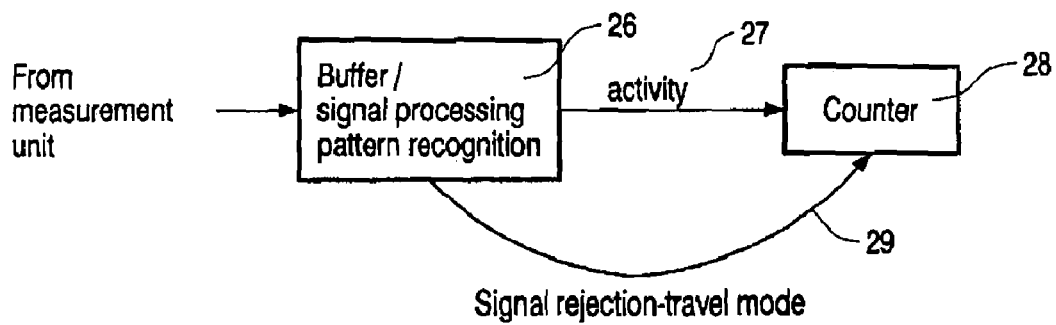
FIG. 6 illustrates part of a system embodying the present invention.

This is illustrated in FIG. 6, in which the processor 11 includes a buffer or signal processing or pattern recognition unit 26 which supplies activity signals 27 to a counter 28. The processor 11 also provides a signal rejection signal 29 to the counter in those circumstances when external motion effects are detected.

It will be appreciated that in the above description, the term "external motion effects" relates to effects on the motion detectors which are not directly attributable to the wearer of the activity monitor. These effects can be produced by, for example, vehicles elevators and the like. The present invention serves to remove erroneous measurements which are caused by such external motion effects.

It will be readily appreciated that the accelerometers are merely preferred motion sensors, and that any appropriate motion sensor could be used in an embodiment of the present invention and achieve the advantages of the present invention.

It is emphasised that the term "comprises" or "comprising" is used in this specification to specify the presence of stated features, integers, steps or components, but does not preclude the addition of one or more further features, integers, steps or components, or groups thereof.

The invention claimed is:

1. An activity monitor f or attachment to an entity, the monitor comprising:
    a measurement unit including one or more motion sensors operable to produce respective sensor signals indicative of motion experienced thereby; and
    a processor operable to:
        receive the sensor signals from the measurement unit;
        process the sensor signals in accordance with a predetermined method; and
        apply a correction calculation to the sensor signals to form corrected signals, in order to remove external motion effects from the sensor signals.

2. The activity monitor claimed in claim 1, wherein the processor is operable to store the corrected signals.

3. The activity monitor claimed in claim 1, wherein the external motion effects are caused by vehicular travel.

4. The activity monitor claimed in claim 1, wherein the processor is operable to detect presence of the external motion effects and to apply the correction calculation upon detection of the external motion effects.

5. A method of monitoring activity of an entity using a plurality of motion sensors which are operable to produce respective sensor signals indicative of motion experienced thereby, the method comprising the acts of:
    receiving the sensor signals;
    processing the signals in accordance with a predetermined method; and
    applying a correction calculation to the sensor signals to form corrected signals in order to remove external motion effects from the sensor signals.

6. The method claimed in claim 5, comprising the step of storing the corrected signals.

7. The method claimed in claim 5, wherein the external motion effects are caused by vehicular travel.

8. The method claimed in claim 5, comprising monitoring the external motion effects and applying the correction calculation upon detection of the external motion effects.

9. A monitor for attachment to an entity, the monitor comprising:
    means for generating sensor signals indicative of motion of the entity;
    means for processing the sensor signals in accordance with a predetermined method; and
    correction means for applying a correction calculation to the sensor signals to form corrected signals in order to remove external motion effects from the sensor signals.

10. The monitor of claim 9 comprising means for storing the corrected signals.

11. The monitor of claim 9, wherein the external motion effects are caused by vehicular travel.

12. The monitor of claim 9, further comprising detection means for detecting presence of the external motion effects; wherein the correction means is operable to apply the correction calculation upon detection of the external motion effects by the detection means.

* * * * *